United States Patent [19]

Sada et al.

[11] Patent Number: 5,147,537

[45] Date of Patent: Sep. 15, 1992

[54] CARRIER FOR AFFINITY CHROMATOGRAPHY IMMOBILIZED WITH ANTIBODIES

[75] Inventors: Eizo Sada; Shigeo Katoh, both of Kyoto; Akihiko Kondo, Kohshoku; Masaaki Kishimura, Kishiwada, all of Japan

[73] Assignee: Chisso Corporation, Osaka, Japan

[21] Appl. No.: 827,917

[22] Filed: Jan. 31, 1992

Related U.S. Application Data

[63] Continuation of Ser. No. 317,561, Mar. 1, 1989, abandoned.

[30] Foreign Application Priority Data

Mar. 10, 1988 [JP] Japan .................... 63-57299

[51] Int. Cl.$^5$ .............................. B01D 15/08
[52] U.S. Cl. .................... 210/198.2; 210/502.1; 210/635; 210/656; 502/403; 530/413
[58] Field of Search ............. 210/635, 656, 198.2, 210/502.1; 502/403; 530/413, 417

[56] References Cited

U.S. PATENT DOCUMENTS

| | | | |
|---|---|---|---|
| 4,177,038 | 12/1979 | Biebricher | 210/635 |
| 4,179,337 | 12/1979 | Davis et al. | 435/181 |
| 4,216,083 | 8/1980 | Dale | 210/635 |
| 4,361,509 | 11/1982 | Zimmerman | 530/387 |
| 4,447,328 | 5/1984 | Kamiyama | 210/656 |
| 4,496,689 | 1/1985 | Mitra | 530/395 |
| 4,579,661 | 4/1986 | Gustafsson | 210/635 |
| 4,814,098 | 3/1989 | Inada | 252/62.56 |

FOREIGN PATENT DOCUMENTS 0011837 11/1979 European Pat. Off. .......... 210/198.2
0184454 12/1985 European Pat. Off. .......... 210/198.2

OTHER PUBLICATIONS

Hackh's Chemical Dictionary, Fourth Edition, McGraw Hill New York, 1972, pp. 192-193.

Abuchowski et al, "Effect of Covalent Attachment of Polyethylene Glycol on Immunogencity and Circulating Life of Bovine Liver Catalase", The Journal of Biological Chemistry, 252, No. 11, pp. 3582-3586 (1977).

Abstracts of Japanese Biochemistry Symposium of the Japanese Biochemical Society, 1986, 58, No. 8 (1986).

Sada et al, "Effects of Coupling Method and Ligand Concentration on Adsorption Equilibrium in Immuno-Affinity Chromatography", Journal of Chemical Engineering of Japan, 1900, No. 6, pp. 502-506 (1986).

Experiment and Application of Affinity Chromatography, published by Kodansha, pp. 32, 33, 64-67, 70-75 (1976).

Primary Examiner—Ernest G. Therkorn
Attorney, Agent, or Firm—Leydig, Voit & Mayer

[57] ABSTRACT

The present invention relates to a carrier for affinity chromatography comprising an insoluble carrier and antibodies which are modified by activated polyethyleneglycol and immobilized on the insoluble carrier, the antibodies being modified by activated polyethylene glycol at a location other than at an immobilizing site.

6 Claims, 1 Drawing Sheet

CARRIER FOR AFFINITY CHROMATOGRAPHY IMMOBILIZED WITH ANTIBODIES

This application is a continuation of application Ser. No. 07/317,561, filed Mar. 1, 1989, now abandoned.

BACKGROUND OF THE INVENTION

The present invention relates to a carrier for affinity chromatgraphy.

The rapid development of biotechnology enables production of various materials having value different from conventional industrial techniques. Namely, with the development of genetic engineering, cell fusion techniques and the like, many techniques for production of useful materials by using their biological function are known. The efficient technique of high purification is a most important matter in laboratories and in factories. For example, gene manipulation has enabled production of trace amounts of physiological active materials such as hormones, lymphokines and the like on an industrial level. However, separation and purification methods involving efficiently and stably separating these materials and removing impurities are desired. As such separation and purification methods, gel filtration, ion exchange and the like have been utilized. These methods need operations having many steps for obtaining materials of adequate purity in high cost and in low yields.

Fundamentally, it is considered to fit the purpose that specific molecular recognition in a cell is used for the separation of such materials which develop physiological function in vivo.

By using specific affinity between special biochemical materials such as an enzyme and an inhibitor an, enzyme and a substrate, an antigen and an antibody a, hormone and a receptor and the like, affinity chromatography can separate these materials. Thus, the technique of affinity chromatography becomes widely used to separate and purify these materials. As the technique using the reaction between an antigen and an antibody, there is immuno affinity chromatography characterized in that the biological affinity specificity is very high. According to this technique, the desired materials to be purified are selectively adsorbed on adsorbent which is obtained by binding an antibody for the desired material as a ligand to an insoluble carrier. The immuno affinity chromatography is applicable to protein, glycoprotein, peptide, enzyme, peptide type hormone and the like, antibodies of which can be produced.

In conventional immuno affinity chromatography, antibodies of glycoprotein are drawn from blood in which antigens are immunized or introduced in mammals such as rabbits, horses, cows, and goats, the resulting antibodies are purified by gel filtration, protein A affinity chromatography and the like, and the antibodies are immobilized on an insoluble substrate. Then, through the specific binding ability between protein as the antibodies and the antigens, the antigens are purified by an immunological method. As the binding of the antibodies and the antigens is comparatively strong, the complex obtained by the reaction is stable. The binding is reversible, and the antigens are dissociated from the immobilized antibodies and purified by changing their conditions.

The antibodies which are used in the above described conventional techniques are protein. The sample liquids containing the antigens mostly contain proteolytic enzyme (protease). For this reason, immobilized antibodies are degraded by the protease, and the binding activity of the antigen of the afinity chromatography is lost. Antibodies are frequently available only at high prices or in slight amounts. It becomes important to use these antibodies efficiently, i.e., continuously without their inactivation.

SUMMARY OF THE INVENTION

An object of the present invention is to provide a carrier for affinity chromatography on which antibodies are immobilized, and which is used continuously without loss of their activity.

Another object of the present invention is to provide a preparation method of a carrier for affinity chromatography on which antibodies are immobilized.

The present invention resides in a carrier for affinity chromatography comprising immobilizing antibodies which are chemically modified by activated polyethylene glycol (abbreviated as "PEG" hereinafter) on the insoluble carrier at a location other than at an immobilizing site.

DETAILED DESCRIPTION OF THE INVENTION

As an example of activated PEG, there is a condensed material of methoxy polyethylene glycol and cyanuric chloride. The material which is used in examples described below is obtained by the preparatory method of A. Abucowski: Journal of Biological Chemistry, vol. 25, pp 3582 (1977).

The method in which antibodies are chemically modified by this activated PEG is as follows:

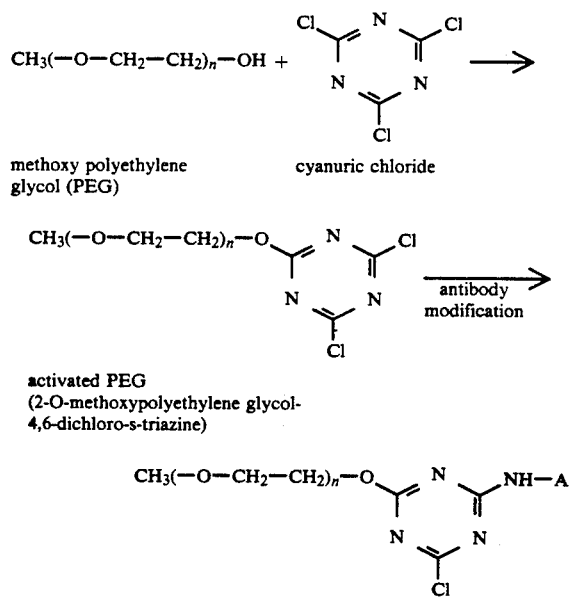

activated PEG
(2-O-methoxypolyethylene glycol-4,6-dichloro-s-triazine)

(In the above formula, A is an antibody).

Namely, methoxy PEG and cyanuric chloride are reacted and activated PEG is obtained. Then, an antibody is added to the reactant, and an antibody which is modified by the activated PEG can be obtained.

Furthermore, the following material can be used as the other activated PEG (Lecture Point Collection of Biochemical Assembly in 1986 4P-4M11, Japan).

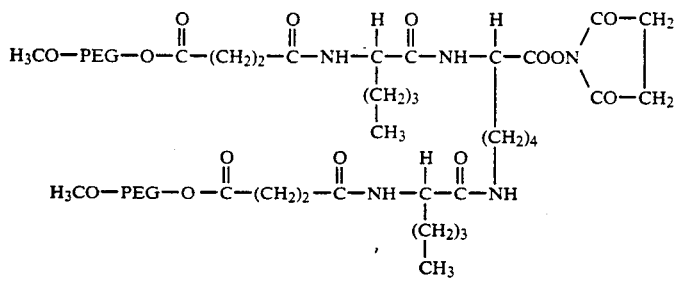

PEGs having various molecular amounts are exemplified, but the present invention especially is not limited to these PEGs.

When antibodids which are modified by the activated PEG are immobilized on a carrier, the protease resistance becomes greater than that of unmodified antibodies. As the acivity of an affinity chromatography column is kept for a long time, the purification with affinity chromatography can be conducted over a long period, so that it is economically effective. It is not found in conventional techniques that a ligand is modified to increase a ligand efficiency as in the technique of the present invention, so that the latter technique is epochal as a separation and purification method.

The preparation methods of a carrier on which activated PEG-modified antibodies are immobilized are exemplified in the following methods, but any methods can be used in the present invention.

(a) Activated PEG-modified antibodies are prepared, and the resulting antibodies are immobilized on a carrier, the location of the PEG modification being other than at the immobilizing site.

(b) Antibodies are firstly immobilized on a carrier, and then the antibodies are modified with activated PEG at a location other than the site of immobilization.

(c) In the method of (a) or (b), the antibodies are previously blocked by antigens.

The methods for immobilizing antibodies on carriers are not specially limited, for example, the methods described in "Experiment and Application of Affinity Chromatography", edited by Kodansha in Tokyo, Japan (1976), namely, techniques of halogenated cyanogens, epichlorohydrin, bisepoxide, hydrazide derivatives can be used. Carriers used in the present invention are for example cellulose, dextran, agarose, polyacrylamide, porous glass and the like, etc., but are not limited thereto.

Furthermore, the antibodies used in the production of the carriers for affinity chromatography of the present invention can be polyclonal antibodies or monoclonal antibodies.

The merits of the invention are follows.

According to the present invention, it is difficult to degrade the antibodies immobilized on the carrier for affinity chromatography by using proteases, and the activity is kept by repetition of the procedure.

Figure 1:
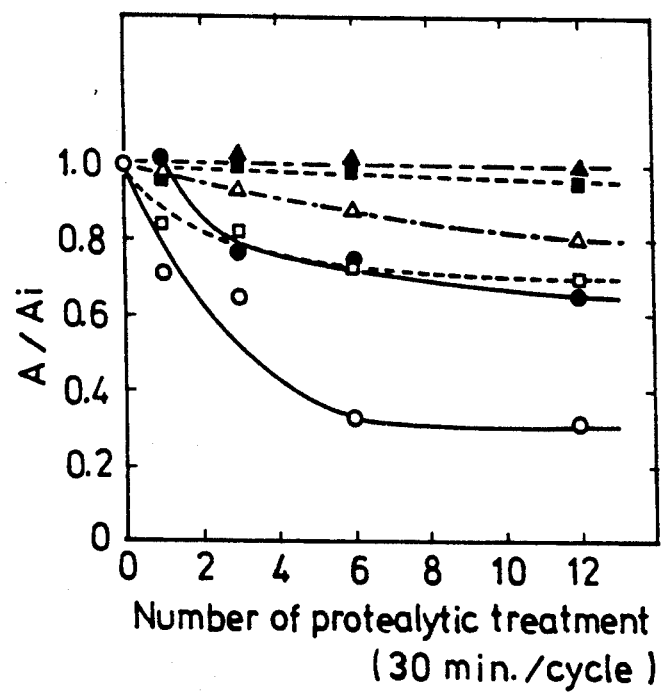
FIG. 1 is a graph showing the relation of lowering of activation of the carrier for affinity chromatography of the present invention comprising an insoluble carrier and antibodies which are modified by activated polyethylene glycol and immobilized on the insoluble carrier, and the carrier for affinity chromatography comprising an insoluble carrier and antibodies which are not modified by activated polyethyleneglycol but immobilized on the insoluble carrier, by repeating the treatment with several kinds of proteases.

Furthermore, in FIG. 1, the relation of lowering of activation of the unmodified and immobilized antibodies to pronase treatment is shown by an open circle, the relation of lowering of activation of the unmodified and immobilized antibodies to tripsin treatment is shown by an open triangle, the relation of lowering of activation of the unmodified and immobilized antibodies to pepsin treatment is shown by an open square.

the relation of lowering of activation of the modified and immobilized antibodies to pronase treatment is shown by a black circle, the relation of lowering of activation of the modified and immobilized antibodies to the tripsin treatment is shown by a black triangle, the relation of lowering of activation of the modified and immobilized antibodies to the pepsin treatment is shown by a black square.

Figure 2:
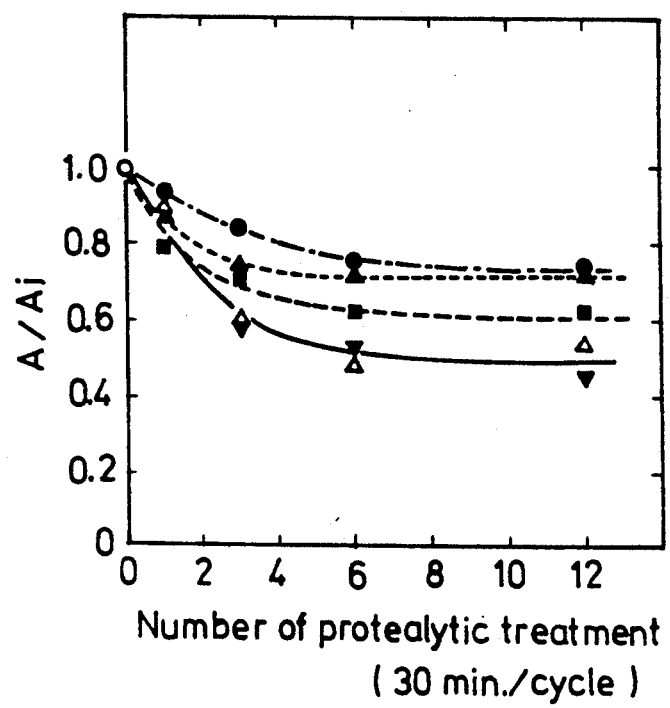
FIG. 2 is a graph showing the relation of lowering of activation of the antibodies which are immobilized on an insoluble carrier and the modification mole ratio of the activated PEG, by repeating the treatment with pronase. In these figures, Ai shows the BSA-adsorbed amount (mg/ml-bed) before the treatment with protease, and A shows the BSA-adsorbed (BSA means bovine serum albumin in the specification) amount (mg/ml-bed) after the treatment with protease.

In FIG. 2, the relation of lowering of activation of the unmodified and immobilized antibodies to pronase treatment is shown by an open triangle, the relation of lowering of activation of the immobilized antibodies which is modified by adding activated PEG in a mole ratio of 3 to the pronase treatment is shown by a black circle, the relation of lowering of activation of the immobilized antibodies which is modified by adding activated PEG in a mole ratio 1 to pronase treatment is shown by a black triangle, the relation of lowering of activation of the immobilized antibodies which is modified by adding activated PEG in a mole ratio 0.7 to pronase treatment is shown by a black square, the relation of lowering of activation of the immobilized antibodies which is modified by adding activated PEG in a mole ratio 0.5 to pronase treatment is shown by a black reverse triangle.

DETAILED DESCRIPTION OF PREFERRED EMBODIMENTS

The following examples illustrate the present invention more specifically.

EXAMPLE 1

BSA as antigens is used. After the BSA antibodies are prepared and bound to a carrier, the binding is modified with activated PEG. The protease activity of the modified binding is tested. The details are as follows.

(1) Preparation of anti-BSA-antibodies . . . These are prepared with a rabbit by a common method (e.g., E. Sada, S. Katoh, A. Kondo and A. Kiyokawa: Journal of Chemical Engineering Japan, vol. 19, pp. 502(1986)).

(2) Immobilization of the antibodies to a carrier . . . An antibody solution was obtained by dissolving 5 mg/ml of the antibodies in 0.1M borate buffer +0.5M sodium chloride. As an insoluble carrier, CNBr-Sepharose 4B (trade name, available from Pharmacia Company) is used. The immobilizing technique of the antibodies is conducted by a conventional method (for example, the method described in "Experiment and Application of Affinity Chromatography", edited by Kodansha in Tokyo, Japan (1976)), and the technique is as follows. Two grams of dried CNBr-Sepharose 4B was washed several times with 400 ml of 1 mM hydrochloric acid, and 14 ml of the antibodies was added and allowed to react with the carrier overnight at 4° C. After reaction, the carrier was washed well several times with the same phosphate-buffered solution. Then, 14 ml of 0.1M ethanol-amine solution was added to the carrier and stirred two hours at room temperature. The carrier was drawn out and washed well with the above phosphate buffer.

(3) Modification with activated PEG . . . The antibody-immobilized carrier of (2) was suspended in 70 ml of 0.1M sodium tetraborate aqueous solution, 195 mg of cyanuric chloride-activated PEG was added, and the mixture was stirred for one hour at 5° C. The carrier was drawn out and washed well with 0.1M of sodium tetraborate aqueous solution. In this case, the mol ratio of the added activated PEG was 1.0. Further, the mol ratio is determined by the following formula.

$$\text{mol ratio} = \frac{\text{added activated PEG amount (mol-PEG)}}{\text{number of amino residues in antibody (mol-NH}_2\text{)}}$$

The number of amino residues was determined by a trinitrobenzenesulfonic acid method (TNBS method). In an unmodified antibody-immobilized carrier, no treatment with activated PEG was conducted.

By such a treatment, a carrier for an affinity chromatography binding activated PEG-modified anti-BSA antibodies and a carrier for an affinity chromatography binding anti-BSA antibodies were prepared, and each amount of the antibodies binding to the carriers was 9.0 mg/ml-carrier by taking the ultraviolet absorption spectrum at a wavelength 280 nm.

(4) Determination of the binding amount of antigens (BSA) . . . The antibody-bound carrier prepared by (3) was charged in a column, and a bed having a diameter of 1.8 cm, a height of 2.8 cm and a volume of 7.0 ml, was obtained. 200 ml of BSA solution (0.2 mg/ml, 0.1M phosphate buffer, pH 7.6) was poured in the column, BSA was saturatedly adsorbed and the adsorbed BSA was removed with 0.1N hydrochloric acid. The amount of the removed BSA was determined by taking the ultraviolet absorption spectrum at a wavelength 280 nm, and the amount of BSA on the antibody-bound carrier was calculated before treatment with protease. The operations were performed at 25° C.

(5) Proteolytic treatment . . . The carrier of the column of (4) was dipped in several protease solutions (5 mg/ml; pepsin +0.1M acetate buffer, pH 3.6; trypsin or pronase +0.1M phosphate buffer, pH7.6) for 30 minutes as one cycle, and the treatment was repeated several times. The temperature of the operations was 25° C.

(6) The amount of the bound antigens (BSA) on the carrier after the protealytic treatment . . . Protease resistance was investigated by determining the amount of the bound antigens (BSA) on the carrier after the treatment of each cycle as described in (5). The method for determining the amount of the bound BSA is the same method as in (4).

The results are shown in FIG. 1. In FIG. 1, a vertical axis shows a ratio of BSA-adsorbed amount after the protealytic treatment A to initial BSA-adsorbed amount (mg/ml) before the treatment Ai, and a cross axis shows the number of protealytic treatments. As apparent from the result, in spite of using tripsin and pepsin which inherently specifically cut peptide bonds, the antibodies modified with activated PEG were not degraded, the loss in the BSA-adsorbed amount was low, and the resistance of the antibodies to proteases remained. In using pronase which nonspecifically cuts the peptide bonds, the resistance to the protease of the antibodies modified with activated PEG remarkably increased.

EXAMPLE 2

The resistance of the antibodies to pronase was examined by altering the rate of the modification of the antibodies by changing the mole ratio of the antibodies modified with the activated PEG. The operations described in Example 1 was repeated except that the amount of the activated PEG to be added was changed to 292 mg in case of the mole ratio 3, 68 mg in the mole ratio 0.7 and 49 mg in the mole ratio 0.5.

The results are shown in FIG. 2. It can be seen that the resistance of the antibodies to pronase is apparently increased in the mole ratio above 0.7.

What is claimed is:

1. A carrier for affinity chromatography comprising an insoluble carrier and antibodies immobilized on the insoluble carrier, said antibodies modified by activated polyethylene glycol at a location other than at an immobilizing site.

2. A carrier in accordance with claim 1, wherein the activated polyethylene glycol is a condensed material of methoxy polyethylene glycol and cyanuric chloride.

3. A carrier in accordance with claim 1, wherein the modified antibodies are obtained by reacting methoxy polyethylene glycol and cyanuric chloride and adding an antibody to the obtained activated polyethyleneglycol.

4. A carrier in accordance with claim 1, wherein the antibodies are polyclonal antibodies or monoclonal antibodies.

5. A carrier in accordance with claim 1, wherein the antibodies are immobilized on the carrier with a halogenated cyanogen, epichlorohydrin, bisepoxide or hydrazide derivative.

6. A carrier in accordance with claim 1, wherein the insoluble carrier is selected from the group of cellulose, dextran, agarose, polyacrylamide and porous glass.

* * * * *